United States Patent
Schlebusch

(10) Patent No.: US 12,257,424 B2
(45) Date of Patent: Mar. 25, 2025

(54) IMPLANTABLE VENTRICULAR ASSIST SYSTEM AND METHOD FOR OPERATING SAME

(71) Applicant: KARDION GMBH, Stuttgart (DE)

(72) Inventor: Thomas Alexander Schlebusch, Renningen (DE)

(73) Assignee: KARDION GMBH, Stuttgart (DE)

( * ) Notice: Subject to any disclaimer, the term of this patent is extended or adjusted under 35 U.S.C. 154(b) by 1004 days.

(21) Appl. No.: 15/734,342

(22) PCT Filed: Jun. 6, 2019

(86) PCT No.: PCT/EP2019/064779
§ 371 (c)(1),
(2) Date: Jul. 30, 2021

(87) PCT Pub. No.: WO2019/234148
PCT Pub. Date: Dec. 12, 2019

(65) Prior Publication Data
US 2021/0346675 A1    Nov. 11, 2021

(30) Foreign Application Priority Data

Jun. 6, 2018 (DE) ...................... 10 2018 208 913.2

(51) Int. Cl.
*A61M 60/523* (2021.01)
*A61M 60/13* (2021.01)
(Continued)

(52) U.S. Cl.
CPC .......... *A61M 60/13* (2021.01); *A61M 60/178* (2021.01); *A61M 60/216* (2021.01);
(Continued)

(58) Field of Classification Search
CPC .. A61M 2205/3317; A61M 2205/3375; A61M 60/13; A61M 60/178; A61M 60/216; A61M 60/523; A61M 60/816
See application file for complete search history.

(56) References Cited

U.S. PATENT DOCUMENTS

| 3,088,323 A | 5/1963 | Welkowitz et al. |
| 4,023,562 A | 5/1977 | Hynecek et al. |
| (Continued) | | |

FOREIGN PATENT DOCUMENTS

| CA | 3 122 415 | 7/2020 |
| CN | 1192351 A | 9/1998 |
| (Continued) | | |

OTHER PUBLICATIONS

Vollkron et al., "Advanced Suction Detection for an Axial Flow Pump", Artificial Organs, 2006, vol. 30, No. 9, pp. 665-670.
(Continued)

*Primary Examiner* — Jon Eric C Morales
(74) *Attorney, Agent, or Firm* — Knobbe, Martens, Olson & Bear, LLP

(57) ABSTRACT

The invention relates to a method for operating an implanted, ventricular assist system (2), comprising the following steps: a) determine a first impedance parameter at a first point in time by means of the assist system (2), b) determine a second impedance parameter at a second point in time by means of the assist system (2), c) at least determine a change of the impedance parameter using the first impedance parameter and the second impedance parameter, or compare at least the first or second impedance parameter to a threshold value.

18 Claims, 3 Drawing Sheets

(51) Int. Cl.
*A61M 60/178* (2021.01)
*A61M 60/216* (2021.01)
*A61M 60/816* (2021.01)

(52) U.S. Cl.
CPC ........ *A61M 60/523* (2021.01); *A61M 60/816* (2021.01); *A61M 2205/3317* (2013.01); *A61M 2205/3375* (2013.01)

(56) References Cited

U.S. PATENT DOCUMENTS

| | | |
|---|---|---|
| 4,559,952 A | 12/1985 | Angelsen et al. |
| 4,680,730 A | 7/1987 | Omoda |
| 4,781,525 A | 11/1988 | Hubbard et al. |
| 4,888,011 A | 12/1989 | Kung et al. |
| 4,889,131 A | 12/1989 | Salem et al. |
| 4,902,272 A | 2/1990 | Milder et al. |
| 5,045,051 A | 9/1991 | Milder et al. |
| 5,269,811 A | 12/1993 | Hayes |
| 5,289,821 A | 3/1994 | Swartz |
| 5,456,715 A | 10/1995 | Liotta |
| 5,527,159 A | 6/1996 | Bozeman, Jr. et al. |
| 5,581,038 A | 12/1996 | Lampropoulos |
| 5,613,935 A | 3/1997 | Jarvik |
| 5,662,115 A | 9/1997 | Torp |
| 5,676,651 A | 10/1997 | Larson, Jr. et al. |
| 5,720,771 A | 2/1998 | Snell |
| 5,752,976 A | 5/1998 | Duffin et al. |
| 5,766,207 A | 6/1998 | Potter et al. |
| 5,827,203 A | 10/1998 | Nita |
| 5,865,759 A | 2/1999 | Koblanski |
| 5,888,242 A | 3/1999 | Antaki et al. |
| 5,904,708 A | 5/1999 | Goedeke |
| 5,911,685 A | 6/1999 | Siess et al. |
| 5,964,694 A | 10/1999 | Siess et al. |
| 5,980,465 A | 11/1999 | Elgas |
| 6,007,478 A | 12/1999 | Siess et al. |
| 6,024,704 A | 2/2000 | Meador et al. |
| 6,053,873 A | 4/2000 | Govari et al. |
| 6,167,765 B1 | 1/2001 | Weitzel |
| 6,176,822 B1 | 1/2001 | Nix et al. |
| 6,183,412 B1 | 2/2001 | Benkowsi et al. |
| 6,185,460 B1 | 2/2001 | Thompson |
| 6,190,324 B1 | 2/2001 | Kieval et al. |
| 6,210,318 B1 | 4/2001 | Lederman |
| 6,231,498 B1 | 5/2001 | Pfeiffer et al. |
| 6,245,007 B1 | 6/2001 | Bedingham et al. |
| 6,314,322 B1 | 11/2001 | Rosenberg |
| 6,351,048 B1 | 2/2002 | Schob et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,512,949 B1 | 1/2003 | Combs et al. |
| 6,530,876 B1 | 3/2003 | Spence |
| 6,540,658 B1 | 4/2003 | Fasciano et al. |
| 6,540,659 B1 | 4/2003 | Milbocker |
| 6,561,975 B1 | 5/2003 | Pool et al. |
| 6,579,257 B1 | 6/2003 | Elgas et al. |
| 6,602,182 B1 | 8/2003 | Milbocker |
| 6,605,032 B2 | 8/2003 | Benkowsi et al. |
| 6,652,447 B2 | 11/2003 | Benkowsi et al. |
| 6,731,976 B2 | 5/2004 | Penn et al. |
| 6,879,126 B2 | 4/2005 | Paden et al. |
| 6,912,423 B2 | 6/2005 | Ley et al. |
| 6,949,066 B2 | 9/2005 | Bearnson et al. |
| 6,984,201 B2 | 1/2006 | Khaghani et al. |
| 7,010,954 B2 | 3/2006 | Siess |
| 7,022,100 B1 | 4/2006 | Aboul-Hosn et al. |
| 7,024,244 B2 | 4/2006 | Muhlenberg et al. |
| 7,070,555 B2 | 7/2006 | Siess |
| 7,083,588 B1 | 8/2006 | Shmulewitz et al. |
| 7,138,776 B1 | 11/2006 | Gauthier et al. |
| 7,160,243 B2 | 1/2007 | Medvedev |
| 7,175,588 B2 | 2/2007 | Morello |
| 7,177,681 B2 * | 2/2007 | Zhu .................. A61N 1/36842 607/9 |
| 7,238,151 B2 | 7/2007 | Frazier |
| 7,396,327 B2 | 7/2008 | Morello |
| 7,513,864 B2 | 4/2009 | Kantrowitz et al. |
| 7,520,850 B2 | 4/2009 | Brockway |
| 7,527,599 B2 | 5/2009 | Hickey |
| 7,591,777 B2 | 9/2009 | LaRose |
| 7,744,560 B2 | 6/2010 | Struble |
| 7,794,384 B2 | 9/2010 | Sugiura et al. |
| 7,819,916 B2 | 10/2010 | Yaegashi |
| 7,850,593 B2 | 12/2010 | Vincent et al. |
| 7,850,594 B2 | 12/2010 | Sutton et al. |
| 7,856,335 B2 | 12/2010 | Morello et al. |
| 7,862,501 B2 | 1/2011 | Woodward et al. |
| 7,951,062 B2 | 5/2011 | Morello |
| 7,951,129 B2 | 5/2011 | Chinchoy |
| 7,963,905 B2 | 6/2011 | Salmonsen et al. |
| 7,988,728 B2 | 8/2011 | Ayre |
| 8,075,472 B2 | 12/2011 | Zilbershlag et al. |
| 8,190,390 B2 | 5/2012 | Morello et al. |
| 8,211,028 B2 | 7/2012 | Karamanoglu et al. |
| 8,303,482 B2 | 11/2012 | Schima et al. |
| 8,323,173 B2 | 12/2012 | Benkowsi et al. |
| 8,435,182 B1 | 5/2013 | Tamura |
| 8,449,444 B2 | 5/2013 | Poirier |
| 8,545,380 B2 | 10/2013 | Farnan et al. |
| 8,585,572 B2 | 11/2013 | Mehmanesh |
| 8,591,393 B2 | 11/2013 | Walters et al. |
| 8,594,790 B2 | 11/2013 | Kjellstrom et al. |
| 8,622,949 B2 | 1/2014 | Zafirelis et al. |
| 8,657,733 B2 | 2/2014 | Ayre et al. |
| 8,657,875 B2 | 2/2014 | Kung et al. |
| 8,715,151 B2 | 5/2014 | Poirier |
| 8,747,293 B2 | 6/2014 | Arndt et al. |
| 8,849,398 B2 | 9/2014 | Evans |
| 8,864,643 B2 | 10/2014 | Reichenbach et al. |
| 8,864,644 B2 | 10/2014 | Yomtov |
| 8,876,685 B2 | 11/2014 | Crosby et al. |
| 8,882,477 B2 | 11/2014 | Fritz, IV et al. |
| 8,888,728 B2 | 11/2014 | Aboul-Hosn et al. |
| 8,897,873 B2 | 11/2014 | Schima et al. |
| 8,903,492 B2 | 12/2014 | Soykan et al. |
| 9,091,271 B2 | 7/2015 | Bourque |
| 9,297,735 B2 | 3/2016 | Graichen et al. |
| 9,308,305 B2 | 4/2016 | Chen et al. |
| 9,345,824 B2 | 5/2016 | Mohl et al. |
| 9,371,826 B2 | 6/2016 | Yanai et al. |
| 9,427,508 B2 | 8/2016 | Reyes et al. |
| 9,474,840 B2 | 10/2016 | Siess |
| 9,492,601 B2 | 11/2016 | Casas et al. |
| 9,511,179 B2 | 12/2016 | Casas et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,566,374 B2 | 2/2017 | Spence et al. |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,694,123 B2 | 7/2017 | Bourque et al. |
| 9,713,701 B2 | 7/2017 | Sarkar et al. |
| 9,744,282 B2 | 8/2017 | Rosenberg et al. |
| 9,789,236 B2 | 10/2017 | Bonde |
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |
| 9,943,236 B2 | 4/2018 | Bennett et al. |
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |

(56) References Cited

U.S. PATENT DOCUMENTS

| | | |
|---|---|---|
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 10,864,308 B2 | 12/2020 | Muller et al. |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 12,059,559 B2 | 8/2024 | Muller et al. |
| D1,043,730 S | 9/2024 | Lussier et al. |
| D1,043,731 S | 9/2024 | Lussier et al. |
| 12,076,544 B2 | 9/2024 | Siess et al. |
| 12,097,016 B2 | 9/2024 | Goldvasser |
| 12,102,815 B2 | 10/2024 | Dhaliwal et al. |
| 12,144,650 B2 | 11/2024 | Spanier et al. |
| 12,144,976 B2 | 11/2024 | Baumbach et al. |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0022785 A1 | 2/2002 | Romano |
| 2002/0082585 A1 | 6/2002 | Carroll et al. |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2003/0199727 A1 | 10/2003 | Burke |
| 2004/0022640 A1 | 2/2004 | Siess et al. |

(56) References Cited

U.S. PATENT DOCUMENTS

| | | |
|---|---|---|
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0108901 A1 | 5/2006 | Mao-Chin |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0069354 A1 | 3/2007 | Dangelmaier |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0172505 A1 | 7/2011 | Kim |
| 2011/0184301 A1* | 7/2011 | Holmstrom ............ A61B 5/349 600/509 |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0203476 A1 | 8/2012 | Dam |
| 2012/0245404 A1 | 9/2012 | Smith |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0066142 A1 | 3/2013 | Doerr et al. |
| 2013/0072846 A1 | 3/2013 | Heide et al. |
| 2013/0116575 A1 | 5/2013 | Mickle et al. |
| 2013/0144379 A1 | 6/2013 | Najafi et al. |
| 2013/0289334 A1 | 10/2013 | Badstibner |
| 2013/0289376 A1 | 10/2013 | Lang |
| 2013/0303831 A1 | 11/2013 | Evans |
| 2013/0304404 A1 | 11/2013 | Dam |
| 2014/0013852 A1 | 1/2014 | Brown et al. |
| 2014/0030122 A1 | 1/2014 | Ozaki |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0275727 A1 | 9/2014 | Bonde |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decréet al. |
| 2016/0151553 A1 | 6/2016 | Bonde |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1* | 9/2016 | Panescu ................ A61B 5/068 |
| 2016/0302672 A1 | 10/2016 | Kuri |
| 2016/0317043 A1 | 11/2016 | Campo |
| 2016/0338629 A1 | 11/2016 | Doerr |
| 2017/0010144 A1 | 1/2017 | Lenner et al. |
| 2017/0021070 A1 | 1/2017 | Petersen |
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0348470 A1 | 12/2017 | D'Ambrosio et al. |
| 2017/0354812 A1 | 12/2017 | Callaghan et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0110910 A1 | 4/2018 | Rodemerk et al. |

(56) References Cited

U.S. PATENT DOCUMENTS

| | | |
|---|---|---|
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0316209 A1 | 11/2018 | Gliner |
| 2018/0326131 A1 | 11/2018 | Muller et al. |
| 2018/0333059 A1 | 11/2018 | Casas |
| 2018/0353667 A1 | 12/2018 | Moyer et al. |
| 2018/0369469 A1 | 12/2018 | Le Duc De Lillers et al. |
| 2019/0001038 A1 | 1/2019 | Yomtov et al. |
| 2019/0054223 A1 | 2/2019 | Frazier et al. |
| 2019/0083690 A1 | 3/2019 | Siess et al. |
| 2019/0192752 A1 | 6/2019 | Tiller et al. |
| 2019/0192753 A1 | 6/2019 | Liu et al. |
| 2019/0209755 A1 | 7/2019 | Nix et al. |
| 2019/0209758 A1 | 7/2019 | Tuval et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0282741 A1 | 9/2019 | Franano et al. |
| 2019/0282744 A1 | 9/2019 | D'Ambrosio et al. |
| 2019/0351117 A1 | 11/2019 | Cambronne et al. |
| 2019/0351118 A1 | 11/2019 | Graichen et al. |
| 2020/0016309 A1 | 1/2020 | Kallenbach et al. |
| 2020/0038567 A1 | 2/2020 | Siess et al. |
| 2020/0060559 A1 | 2/2020 | Edelman et al. |
| 2020/0069857 A1 | 3/2020 | Schwammenthal et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2021/0268264 A1 | 9/2021 | Stotz |
| 2021/0290087 A1 | 9/2021 | Schlebusch |
| 2021/0290930 A1 | 9/2021 | Kasel |
| 2021/0290933 A1 | 9/2021 | Stotz |
| 2021/0339002 A1 | 11/2021 | Schlebusch et al. |
| 2021/0339004 A1 | 11/2021 | Schlebusch et al. |
| 2021/0346674 A1 | 11/2021 | Baumbach et al. |
| 2021/0346676 A1 | 11/2021 | Schlebusch et al. |
| 2021/0346677 A1 | 11/2021 | Baumbach et al. |
| 2021/0346678 A1 | 11/2021 | Baumbach et al. |
| 2021/0378523 A1 | 12/2021 | Budde |
| 2021/0379359 A1 | 12/2021 | Schellenberg |
| 2021/0379360 A1 | 12/2021 | Schellenberg |
| 2021/0393944 A1 | 12/2021 | Wenning |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0105339 A1 | 4/2022 | Nix et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161019 A1 | 5/2022 | Mitze et al. |
| 2022/0361762 A1 | 11/2022 | Lalancette |
| 2023/0173250 A1 | 6/2023 | Stigloher |
| 2023/0191141 A1 | 6/2023 | Wenning et al. |
| 2024/0011808 A1 | 1/2024 | Winzer et al. |
| 2024/0074828 A1 | 3/2024 | Wenning |
| 2024/0245902 A1 | 7/2024 | Schlebusch et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |

(56) References Cited

FOREIGN PATENT DOCUMENTS

| | | |
|---|---|---|
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 4 034 221 | 11/2024 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/005228 | 1/2018 |

(56) References Cited

FOREIGN PATENT DOCUMENTS

| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

Vollkron et al., "Development of a Suction Detection System for Axial Blood Pumps", Artificial Organs, 2004, vol. 28, No. 8, pp. 709-716.
Hertz Ph.D et al, "Ultrasonic Engineering in Heart Diagnosis", The American Journal of Cardiology, Jan. 1967, vol. 19, No. 1, pp. 6-17.
Kong et al., "A Stein Equation Approach for Solutions to the Diophantine Equations," 2010 Chinese Control and Decision Conference, Xuzhou, May 26, 2010, pp. 3024-3028.
McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.
Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.
Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.
Koseli et al., "Online Viscosity Measurement of Complex Solutions Using Ultrasound Doppler Velocimetry", Turk J Chem, Jan. 2006, vol. 30, pp. 297-305.
International Search Report and Written Opinion received in PCT Application No. PCT/EP2019/064779, dated Sep. 3, 2019 in 14 pages.
International Preliminary Report on Patentability and Written Opinion received in PCT Application No. PCT/EP2019/064779, dated Oct. 23, 2020 in 28 pages.
Atkinson et al., "Pulse-Doppler Ultrasound and Its Clinical Application", The Yale Journal of Biology and Medicine, 1977, vol. 50, pp. 367-373.
Leguy et al., "Assessment of Blood Volume Flow in Slightly Curved Arteries from a Single Velocity Profile", Journal of Biomechanics, 2009, pp. 1664-1672.
Lombardi et al., "Flow Rate Profiler: an instrument to measure blood velocity profiles", Ultrasonics, 2001, vol. 39, pp. 143-150.
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
"Understanding Hot-Wire Anemometry", Advanced Thermal Solutions, Inc., 2007, pp. 13-17.
Vieli, A., "Doppler Flow Determination", BJA: British Journal of Anaesthesia, 1988, vol. 60, pp. 107S-112S.
Yuanyuan et al., "Characteristics Analysis for Doppler Ultrasound Blood Flow Signals", China Medical Device Information, 5(1), Feb. 28, 1999, pp. 36-42.
Zhang, Dabiao et al., "Design of Microwave Velocity and Distance Monitor System", Instrument Technique and Sensor, Hebei Normal University, Apr. 25, 2004, pp. 3.
HeartMate 3™ Left Ventricular Assist System, Instructions for Use, Thoratec Corporation, Aug. 2017, p. 536. [Uploaded in 3 parts].

* cited by examiner

IMPLANTABLE VENTRICULAR ASSIST SYSTEM AND METHOD FOR OPERATING SAME

BACKGROUND

Field

The invention relates to a method for operating an implanted ventricular assist system, a processing unit and an implantable ventricular assist system. The invention is used in particular for (fully) implanted left heart assist systems (LVAD [Left Ventricular Assist Device]).

Description of the Related Art

Implanted left heart assist systems (LVADs) mainly exist in two design variants. On the one hand, there are (percutaneous) minimally-invasive left heart assist systems. The second variant are left heart assist systems invasively implanted under the rib cage. The first variant circulates blood directly from the left ventricle into the aorta, since the (percutaneous) minimally invasive left heart assist system is positioned in the center of the aortic valve. The second variant circulates the blood from the apical region from the left ventricle via a bypass tube into the aorta.

The task of a cardiac assist system is to circulate blood. The so-called heart-time-volume (Herz-Zeit-Volumen [HZV], usually stated in liters per minute) has high clinical relevance in this case. In other words, the heart-time volume affects the total volume flow of blood from a ventricle, particularly from the left ventricle to the aorta. Accordingly, the initial task is to determine this parameter as a metrology value while a cardiac assist system is in operation.

Depending on the level of assistance, which describes the share of the volume flow from the ventricle to the aorta conveyed by a circulation means, such as a pump of the assist system, a certain volume flow reaches the aorta via the physiological path through the aortic valve. The heart-time volume or the total volume flow ($Q_{HZV}$) from the ventricle to the aorta is therefore usually the sum of the pump volume flow ($Q_p$) and the aortic valve volume flow ($Q_a$).

An established method for determining the heart-time volume ($Q_{HTV}$) in the clinical setting is the use of dilution methods, which, however, all rely on a catheter inserted transcutaneously and therefore can only provide heart-time volume measurement data during cardiac surgery. An established method for measuring the pump volume flow ($Q_p$) is the correlation of the operating parameters of the assist system, predominantly the electrical power consumption, possibly supplemented by further physiological parameters, such as the blood pressure. The integration of dedicated ultrasound measurement technology into an assist system has also already been proposed.

SUMMARY

A (fully) implanted recording of the heart-time volume, i.e., of $Q_{HZV}$, in particular by the assist system itself, has not yet been suggested or implemented. Fully implanted in this case means, in particular, that the means required for recording are completely in the patient's body and remain there. This makes it possible to record the heart-time volume even outside of heart surgery.

Impedance cardiography is a method for determining the so-called cardiac output using extracorporeal impedance measurements. Four electrodes are used for this. A small alternating current is fed in by two electrodes; the resulting voltage drop is measured with two additional electrodes. Since blood has a higher conductivity than the surrounding tissue, especially compared to the air-filled lung, the blood volume change in the thorax can be detected as an impedance change over a cardiac cycle. Impedance cardiography is used extracorporeally, usually with ring or adhesive electrodes around the neck and abdomen.

The use of left ventricular impedance together with the electrocardiogram to detect abnormal mechanical contractions of the heart muscle in LVAD patients is also known. An intracardiac ECG is in this case combined with a left ventricular impedance measurement to detect abnormal contractions of the ventricle. The measurement is synchronized by the ECG. The measurement is qualitative, and volume is not determined.

The use of impedance measurements for quantitative volume determination is known in the area of the bladder volume. Four electrodes are used on the outside of a catheter, which is only inserted into the bladder for measuring purposes and then removed again. It has been shown that the measured impedance is inversely dependent on the volume of the bladder. However, a problem of the method is the strong dependency on the urine conductivity.

Based on this, the invention is based on the task to further improve a method for operating an implanted, ventricular assist system for recording special parameters and to specify a corresponding advantageous system.

To achieve this task, combinations of features described herein are proposed. Advantageous configurations and further developments of the invention are described herein.

According to one aspect of the invention, a method for operating an implanted, ventricular assist system comprises:
 a) determining a first impedance parameter at a first point in time using the assist system,
 b) determining a second impedance parameter at a second time point using the assist system,
 c) determining at least a change in the impedance parameter using the first impedance parameter and the second impedance parameter, or compare at least the first or second impedance parameter to a threshold value.

The assist system preferably serves the purpose of circulating fluid. The ventricular assist system is preferably a cardiac assist system. The method preferably serves to determine a total fluid volume flow (through a cross-section in the region of the assist system) from a ventricle of a heart, in particular from a (left) ventricle of a heart to the aorta in the region of a (fully) implanted, (left) ventricular (heart) assist system, and/or to determine an aortic valve or bypass volume flow that flows past the assist system. The fluid is regularly blood. The assist system is preferably arranged at the exit of the left ventricle of the heart or the left ventricle. The assist system is particularly preferably arranged in the aortic valve position. In particular, the total volume flow is defined as the total volume flow through a blood vessel or through a cross-section of the blood vessel. The blood vessel is, for example, the aorta, particularly in the case of a left heart assist system, or the pulmonary trunk (Truncus pulmonalis) into the two pulmonary arteries, particularly in the case of a right heart assist system. The method is particularly suitable for determining the total heart-time volume (HTV, with formula symbol $Q_{HZV}$) of a patient, in particular with a (fully) implanted left ventricular heart assist system (LVAD) in the aortic valve position and/or through the assist system itself.

The method is based in particular on the integration of a ventricular impedance measurement, in particular impedance spectroscopy into a (left) ventricular (heart) assist system (LVAD), preferably for determining the heart-time volume (HTV) and/or the aortic valve or bypass volume flow. In addition, the procedure may contribute towards determining the level of assistance. The method advantageously makes it possible for the cardiac-time volume and/or the bypass volume flow to be provided outside the surgical scenario with a quality comparable to using a dilution catheter. This is particularly advantageous, since the heart-time volume ($Q_{HZV}$) has a greater clinical relevance than the more commonly used pump volume flow ($Q_p$), which only quantifies the flow through the assist system itself. The solution proposed here is characterized in particular by the use of sensors integrated strictly in the LVAD; for example, no separate ultrasonic cuff is required around the aorta.

In step a), an (at least) first impedance parameter is determined at a first point in time by means of the assist system. A first ventricular volume is preferably determined at a first point in time in step a) by means of an impedance measurement by means of the assist system or by means of the first impedance parameter. In other words, this means in particular that the assist system itself determines, in particular measures, the impedance parameter or the ventricular volume. In step b), an (at least) second impedance parameter is determined at a second point in time by means of the assist system. A second ventricular volume is preferably determined in step b) at a second point in time by means of an impedance measurement by means of the assist system. In other words, this means in particular that in steps a) and b) at least one impedance parameter and/or one ventricular volume is determined over time. The first and second points in time differ from each other. Preferably, the second point in time is after the first point in time. A plurality of impedance parameters or ventricular volumes can be determined at other points in time. Short gaps between the points in time are particularly advantageous for forming a differential to determine the volume flow. The ventricular volume is limited in particular by the ventricular wall or the ventricular chamber wall formed in the manner of a bag and by two heart valves, one of which is also called an aortic valve. The ventricular volume is essentially determined by the fluid volume (here, in particular, blood volume) in the ventricle. The differences in ventricular volume result in particular from the contraction of the heart muscle and usually contribute to the circulation of blood by the cardiovascular system of humans, or patients if applicable.

The impedance parameter can for example be a (bio) impedance, in particular of fluid and/or tissue in the region of the assist system. Raw data of an analog/digital transducer (unitless values) of an impedance measurement device can also serve as impedance parameters. The impedance parameter is preferably a ventricular impedance. In other words, this means in particular that a ventricular impedance is determined in steps a) and b). Ventricular impedance is regularly a function of ventricular volume, in particular the fluid volume in the ventricle, and fluid conductivity (in particular blood conductivity). In addition, the muscles surrounding the ventricle can also provide an impedance component. The influence of the blood conductivity can be determined by separate impedance measurement in a known sample volume. In particular, a measurement in the defined volume of the (inlet) cannula is a candidate in this case. The impedance measurement serves in particular to determine the pulsatile volume change of the ventricle during the systole. In an advantageous embodiment, the impedance data can be validated by means of pressure sensor data.

It is particularly preferred that the impedance of the ventricle (of unknown volume) is determined by electrodes integrated into and/or in the assist system. The electrodes (for ventricular impedance measurement) are preferably arranged on or in the surface, in particular on or in the outer surface of the assist system (circumferentially). The electrodes are particularly preferably arranged on or in the outer surface of a (n) (inlet) cannula of the assist system (circumferentially).

In step c), a change (over time) of the impedance parameter is determined using the first impedance parameter and the second impedance parameter. Step c) can alternatively or cumulatively compare at least the first or second impedance parameter to a threshold value. A change (over time) of a ventricular impedance is preferably determined using the first impedance parameter and the second impedance parameter. The threshold value is preferably a (pre-) defined and/or constant threshold value. The threshold value can for example be determined, in particular specified, with a calibration (in vivo) as a particularly lower threshold for the impedance parameter or corresponding raw data values. The lower threshold is dimensioned in particular such that a collapse of the ventricle and/or a suction effect, which leads to a suctioning of the assist system to the inner ventricle wall, can be avoided. Step c) preferably determines a change (over time) in the ventricular volume using the first impedance parameter and/or the first ventricular volume and the second impedance parameter and/or the second ventricular volume. Step c) can alternatively or cumulatively compare the first and/or second impedance parameter and/or ventricular volume to a minimum ventricular volume. The change of the impedance parameter or ventricular volume is in particular determined if the assist system is implanted in a patient with partial assistance (low to high assistance level). The comparison to the threshold or the minimum ventricular volume is in particular made if the assist system is implanted in a patient with full assistance (assistance level=100%). If only one comparison with the threshold or minimum ventricular volume is to be performed, one of steps a) or b) can be omitted. In addition, the determination of the change and the comparison can also be performed cumulatively, in particular simultaneously, or at least partially in parallel, for example in a recovering short-term (full) assistance patient. Alternatively or cumulatively to the lower threshold or minimum ventricular volume, an upper threshold value or maximum ventricular volume can be specified for the comparison. The upper threshold value and/or the minimum ventricular volume is dimensioned in particular such that an excessive load, in particular an expansion of the ventricular wall, can be avoided.

In patients with partial assistance, the change in the impedance parameter or the ventricular volume during the systole (contraction or blood outflow phase of the heart) can contribute toward transporting blood through the cardiovascular system, or in other words contribute toward maintaining or increasing the total fluid volume flow from the ventricle or the heart-time volume. In these patients in particular, the determination of the change of the impedance parameter or ventricular volume is particularly important. The pulsatile impedance parameters or volume change of the ventricle is preferably determined during the systole. In other words, this means in particular that in step c) the (pulse or muscle-induced) change in the impedance parameter or ventricular volume is preferably determined during the systole. Particularly preferably, the difference between the impedance parameter or ventricular volume is determined at the start of the systole, and between the impedance parameter or ventricular volume at the end of the systole. For this purpose, the first point in time can for example be the start of the systole and the second point in time the end of the systole. In this exemplary illustration, however, it should be taken into account that the sampling rate of the impedance parameter or ventricular volume should be high enough to fulfill the Nyquist theorem for expected ventricular contractions, for example 60 1/s.

In patients with full assistance (especially with a continuously operational assist system), the change in impedance parameter or ventricular volume plays a rather subordinate role in particular. Rather, care should be taken in these patients to ensure that the impedance parameter or the ventricular volume does not fall below a lower threshold value or a minimum ventricular volume. The minimum ventricular volume is preferably a defined or predetermined and/or constant minimum ventricular volume. The minimum ventricular volume is dimensioned in particular such that a collapse of the ventricle and/or a suction effect, which leads to a suctioning of the assist system to the inner ventricle wall, can be avoided. The comparison can be performed in the processing unit. For this purpose, the measuring device can provide the (first and/or second) impedance parameter or the (first and/or second) ventricular volume as the initial value of the processing unit. The impedance parameter or the ventricular volume can represent a control parameter for the assist system, which is preferably held above the lower threshold value or the minimum ventricular volume. In addition, an impedance parameter to threshold or ventricular volume to minimum ventricular volume difference can represent a control parameter for the assist system. A processing unit of the assist system can provide this control parameter as an output parameter, in particular of a control unit of the assist system, which preferably regulates the output of an electric motor of the assist system and thus also in particular the (blood) circulation volume of the assist system. For example, the circulation volume of the assist system can be reduced if there is a risk of suctioning of the ventricular wall. In addition, the circulation volume of the assist system can be increased, for example, if there is a risk of excessive expansion of the ventricular wall.

In particular, if a plurality of impedance parameters or ventricular volumes are determined in steps a) and b), it is particularly advantageous that at least one model graph is adjusted to the impedance parameters or ventricular volumes. It is then also preferred if processing continues with the model parameters or the at least one model graph.

According to an advantageous embodiment, it is proposed that a ventricular volume is determined with the (respective) impedance parameter. In other words, this means in particular that an impedance measurement is carried out to determine the ventricular volume or that a ventricular volume is determined from the impedance measurement. Preferably, the first impedance parameter is used to determine a first ventricular volume, and the second impedance parameter is used to determine a second ventricular volume.

According to a further advantageous embodiment, it is proposed that the (respective) impedance parameters are measured by at least two electrodes arranged on the assist system. The first and the second impedance parameters (the respective ventricular impedance) are particularly preferably measured by at least two, advantageously four electrodes. For this purpose, a (smaller) patient auxiliary current, for example 50 kHz. 100 µA (alternating current) can be used for measurement. The electrodes are also preferably spaced apart from one another such that their detection range or detection volume comprises the ventricular volume. The detection range or the detection volume relates in particular to the region or volume that is covered by the current paths between the electrodes. In other words, this relates in particular to the region or the volume through which or such that the current paths extend between the electrodes. The at least two electrodes preferably comprise at least two electrode pairs, in particular each comprising a current electrode and a voltage measurement electrode. The electrodes of a pair should lie close to each other. However, the pairs should be separated from each other. An arrangement is advantageous wherein the current electrodes are located outside and the voltage measuring electrodes are located inside (in the form of a four-wire measurement). The detection range or the detection volume is generally increased with increasing distance between the electrode pairs. The distance is preferably determined such that the entire volume of the ventricle can be detected as far as possible, but the surrounding tissue and/or surrounding organs, in particular the lungs, are not in the detection range as far as possible.

According to a further advantageous embodiment, it is proposed that an impedance measurement is carried out at different (alternating current) frequencies, in particular for determining the first and/or second impedance parameters. This can advantageously contribute toward reducing the influence of surrounding tissue, in particular the heart muscles, on the impedance measurement. Particularly preferably, a (bio) impedance spectroscopy is performed. Preferably, the frequencies are selected such that the background impedance of the heart muscle can be or is determined, particularly preferably periodically. This background impedance can be taken into account for the impedance measurement of the ventricular volume.

According to an advantageous embodiment, it is proposed that the conductivity of the fluid be determined by an impedance measurement in a defined volume of the assist system. This contributes in particular to the fact that the assist system itself can determine the conductivity of the fluid, which has an influence on the impedance measurement. The defined volume is preferably located inside a (n) (inlet) cannula of the assist system. The defined volume is particularly preferably limited by the inner surface or a part of the inner surface of the cannula of the assist system. In addition, the defined volume (in a direction along the cannula) can be limited by two electrodes. Preferably, at least one of the (limiting) electrodes is in this case arranged on or in the inner surface of the cannula. Furthermore, it is preferred that at least two, advantageously four, electrodes are arranged for conductivity measurement on or in the inner surface of the cannula (circumferentially).

According to an advantageous embodiment, it is proposed that a fluid volume flow that flows through the assist system is also determined. In other words, this relates in particular to a fluid volume flow that only flows through the assist system itself. The fluid volume flow is usually the so-called pump volume flow ($Q_p$), which only quantifies the flow through the support system itself. If this value is known in addition to the total volume flow or heart-time volume ($Q_{HZV}$), the so-called level of assistance can be calculated from the ratio of $Q_p$ to $Q_{HZV}$ (i.e., $Q_p/Q_{HZV}$). To determine the pump volume flow, an established method discussed above in connection with the prior art can be used for measuring the pump volume flow. For example, the pump volume flow can be determined based on differential pressure and motor characteristic field or by explicit Doppler ultrasonic measurement. The pump volume flow is preferably determined by means of an ultrasonic sensor, which can for example be accommodated in a tip of the assist system.

The fluid volume flow graph versus time or the pump volume flow is preferably determined. The latter can be compared to total fluid volume graph over time. The level of assistance can be provided as a control parameter for the assist system.

According to an advantageous embodiment, it is proposed that a total fluid volume flow be determined in the region of the assist system. The total fluid volume flow is preferably determined using the first ventricular volume and the second ventricular volume. In cases in which the total fluid volume flow corresponds essentially to the time-related derivative of the ventricular volume, the total fluid volume flow can be (approximately) determined in the form of a difference ratio, which is the ratio ($\Delta V/\Delta t$) of the ventricular volume difference ($\Delta V$=second ventricular volume–first ventricular volume) to the time difference ($\Delta t$=second point in time (e.g., systole end)–first point in time (e.g., systole start). Cases in which the total fluid volume flow essentially corresponds to the time-related derivative of the ventricular volume can in particular occur with low assistance levels and/or pulsatile operating assist systems, for example controlled by a pressure sensor in the ventricle or an ECG sensor. In addition, an estimate of the total heart-time volume (HZV) can also be made using the measured pump volume flow and the measured ventricular volume. Preferably, the total fluid volume flow or the heart-time volume is calculated by sampling the ventricular volume and the fluid volume flow rate or pump volume flow versus time. The total fluid volume flow or the heart-time volume ($Q_{HZV}$) can generally (at least for continuously operating assist systems) be determined from the following relationship between change of the ventricular volume ($\partial V/\partial t$) versus time and the basic pump volume flow ($Q_{p,diastole}$):

$$Q_{HZV}(t) = Q_{P,Diastole} - \frac{\partial V}{\partial t}$$

The determined total fluid volume flow is preferably provided as a control parameter for the assist system. A processing unit of the assist system can provide this control parameter as an output parameter, in particular of a control unit of the assist system, which preferably regulates the output of an electric motor of the assist system and thus in particular also regulates the (blood) circulation volume of the assist system.

Furthermore, an aortic valve or bypass volume flow ($Q_A$) is preferably determined. Particularly preferably, the bypass flow (aortic valve or bypass volume flow) is quantified as a bypass to the assist system and through the aortic valve by means of the ventricular volume change and pump volume flow:

$$Q_A(t) = \frac{\partial V}{\partial t} + Q_{P,Diastole} - Q_P(t)$$

The bypass volume flow can be provided as a control parameter for the assist system.

According to a further aspect, a processing unit is proposed that is configured for carrying out a method proposed here. The processing unit can comprise a microprocessor, which can access a memory. The processing unit preferably receives data from the measuring device.

According to a further aspect of the invention, an implantable, ventricular assist system is proposed, comprising:

a measuring device, configured for determining a first impedance parameter at a first point in time and a second impedance parameter at a second point in time, a processing unit, configured at least to determine a change of the impedance parameter (over time) using the first impedance parameter and the second impedance parameter or to compare at least the first or second impedance parameter to a threshold value.

The assist system is preferably a left-ventricular heart assist system (LVAD) or a percutaneous, minimally invasive left heart assist system. Furthermore, it is preferred that the assist system can be fully implanted. In other words, this means, in particular, that the means required for sensing, in particular an impedance sensor and/or the pump volume flow sensor, are completely located in the body of the patient and remain there. The assist system is particularly preferably configured and/or suitable for being arranged at least partially in a ventricle, preferably in the left ventricle of a heart, and/or in an aorta, in particular in the aortic valve position.

Furthermore, the assist system preferably comprises a cannula, in particular an inlet cannula, a flow machine, such as a pump and/or an electric motor. The electric motor is regularly a component of the flow machine. The (inlet) cannula is preferably arranged such that in the implanted state it can guide fluid from a (left) ventricle of a heart to the flow machine. The assist system is preferably elongated and/or tubular. Preferably, the inlet cannula and the flow machine are arranged in the region at opposite ends of the assist system.

According to an advantageous embodiment, it is proposed that the measuring device comprises at least two electrodes by which an impedance can be measured. At least four electrodes are preferably provided for the measurement of a ventricular impedance. Particularly preferably, the electrodes are configured and arranged such that the impedance of the (entire) ventricle can be determined.

The details, features, and advantageous embodiments discussed in connection with the method can also occur accordingly in the processing unit and/or the assist system presented here and vice versa. In this respect, reference is made in full to the statements therein regarding the more detailed characterization of the features.

BRIEF DESCRIPTION OF THE DRAWINGS

The solution presented here as well as its technical environment are explained in more detail below with reference to the figures. It should be pointed out that the invention is not to be limited by the exemplary embodiments shown. In particular, unless explicitly stated otherwise, it is also possible to extract partial aspects of the facts explained in the figures and to combine them with other components and/or insights from other figures and/or the present description. The following show schematically.

DETAILED DESCRIPTION

Figure 1:
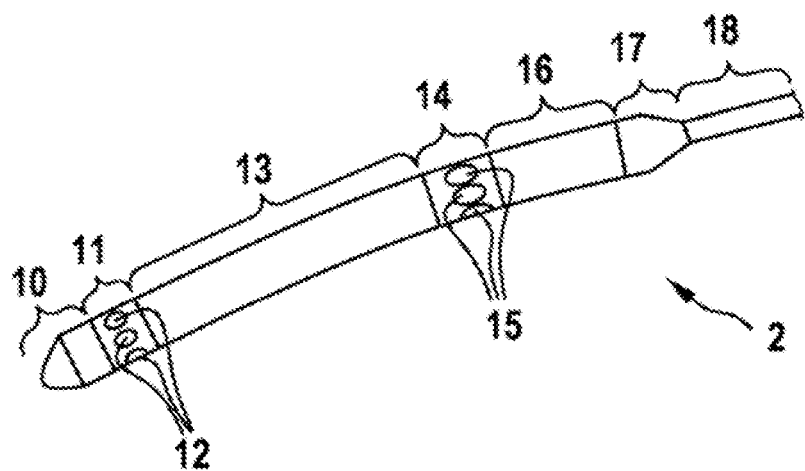
FIG. 1 an implantable assist system,
FIG. 2 an implanted ventricular assist system in a heart,
FIG. 3 the assist system from FIG. 2,
FIG. 4 an implanted ventricular assist system, and
FIG. 5 a schematic process diagram of the described method.

FIG. 1 schematically shows an implantable assist system 2. The assist system 2 is in this case an example of a left ventricular assist system (LVAD). The assist system 2 comprises a tip 10, which can contain sensors, an inlet cage 11 with feed openings 12 for suctioning fluid (here: blood), a flexible cannula 13, an impeller cage 14 with turbine wheel (not shown here) and outlet openings 15 for the blood, an electric motor 16, a rear end 17 (so-called backend), which can contain sensors, and a connection cable 18.

Figure 2:
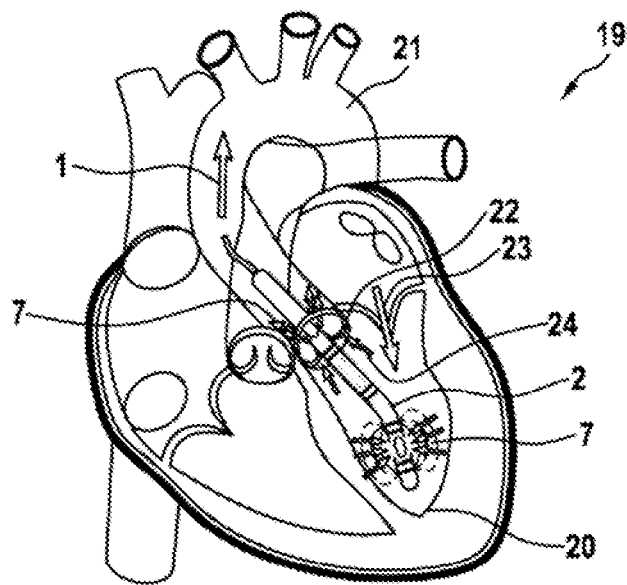

FIG. 2 shows schematically an implanted ventricular assist system 2 in a heart 19. The assist system 2 assists the heart 19 by assisting the circulation of blood from the (left) ventricle 20 into the aorta 21. For this purpose, the assist system 2 is anchored in the aortic valve 22, as illustrated in FIG. 2. At an assistance level of 100%, the assist system 2 (LVAD) circulates the complete blood volume flow. The level of assistance describes the proportion of the volume flow circulated by a conveying means, such as a pump of the assist system 2 or through the assist system 2, to the total volume flow of blood from the ventricle 20 to the aorta 21.

At an assistance level of 100%, the total fluid volume flow 1 from the ventricle 20, the heart valve volume flow 23 into the ventricle 20, and the fluid volume flow 7 through the assist system 2 are therefore identical. The aortic valve or bypass volume flow 24 (formula symbol: $Q_a$) is therefore zero. The total fluid volume flow 1 can also be described as (total) heart-time volume (HZV, formula symbol: $Q_{HZV}$). The fluid volume flow 7 can also be referred to as a so-called pump volume flow (formula symbol: $Q_p$), which only quantifies the flow through the assist system itself. The level of assistance can thus be calculated from the ratio $Q_p/Q_{HZV}$.

For lower levels of assistance and healthier hearts with strong ventricular contraction, the heart 19 continues to fulfill its function to a certain extent, so that a pulsatile volume flow fraction 24 (bypass) through the heart or aortic valve 22 is generated during the systole (heart muscle contracts and by reducing the volume of the ventricle 20 displaces blood into the aorta 21). At the same time, the pressure difference over the assist system 2 decreases, in particular over the normally provided pump (not shown here) of the assist system 2, so that the assist system 2 accordingly also conveys an increased fluid volume flow 7 during the systole.

The solution proposed here is based in particular on detecting the change of the ventricular volume over time by way of an impedance measurement. For a known (or recorded over time) fluid volume flow 7 or pump volume flow ($Q_p$), the otherwise barely measurable aortic valve or bypass volume flow 24 can then be advantageously quantified by determining the differential.

Figure 3:
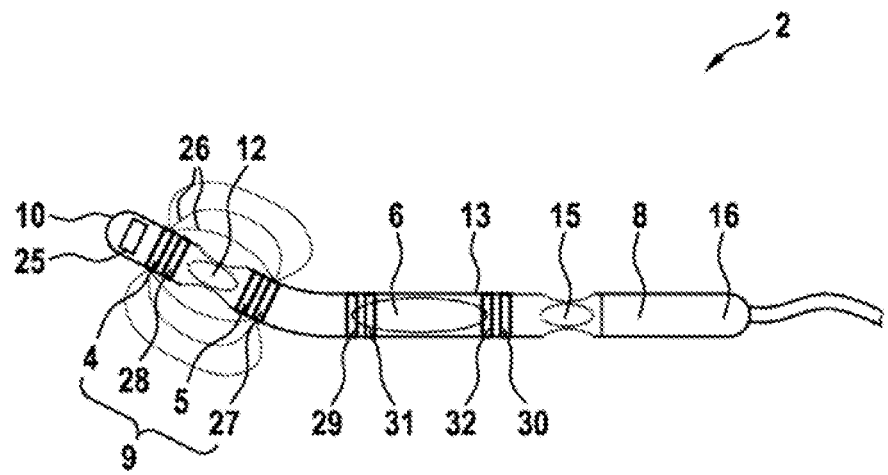

FIG. 3 schematically shows the assist system 2 from FIG. 2. To determine the ventricular volume at a specific point in time, FIGS. 2 and 3 show a realization form by way of a (left ventricular) intracardiac impedance measurement. The impedance measurement has the advantage that the entire fluid or liquid volume and an electrical resistance measurement can be implemented with relatively straightforward technical means. By using four electrodes 4, 5, 27 and 28 (four-wire measurement) as in the example shown here, the impedance measurement is largely independent of the contact resistance of the measurement electrodes, so that the measurement result is also suitable for long-term implantation in the patient. Electrodes 4, 5, 27 and 28 in this case form an exemplary measuring device 9 of the assist system 2. FIG. 3 also illustrates by way of example that an ultrasonic-based pump volume flow sensor 25 can be integrated in the tip 10. The pump volume flow sensor 25 can detect and supply the fluid volume flow 7 and/or the pump volume flow ($Q_p$) over time.

For the impedance measurement, at least two electrodes 4, 27 should be integrated in the region of the ventricle 20, so that the current paths 26 of the measuring current can record the ventricular volume as best as possible. The region of the inlet cage 11 is suited for this purpose, for example proximally and/or upstream and distally and/or downstream of the inlet openings 12. At least two electrodes 4, 27 are technically required to close the electrical circuit. The use of four electrodes 4, 5, 27 and 28 is advantageous, since the influence of the contact impedance from the electrode to the blood can be ignored; long-term changes of the electrode surface therefore have no or only a negligible influence on the measurement result. For example, the current electrodes 4, 27 are preferably placed on the outside and the voltage measurement electrodes 5, 28 between them. The current paths 26 in this case extend from the electrode 4 to the electrode 27 (current electrodes). Equipotential lines that are not shown here form between them, which can be measured at high resistance by the voltage electrodes 28 and 5.

Since the detection volume is dependent in particular on the distance of the measurement pairs (4 and 28 to 5 and 27), it is advantageous to place one pair 4, 28 as distally as possible or in the region of the tip 10 and one pair 5, 27 as proximally as possible or towards the electric motor 16 of the assist system 2. It is advantageous in this case for the measurement quality if all four electrodes 4, 5, 27 and 28 are nevertheless placed in the area of the ventricle 20 and the proximal pair 5, 27 does not move beyond the aortic valve plane into the aorta 21, wherein a measurement would also be conceivable or feasible based on this design.

The measured electrical conductivity between the electrode pairs is a function of the surrounding fluid or fluid volume and its conductivity. A predetermined and/or constant conductivity can be assumed, since the ion concentration in the blood is kept within narrow limits by the kidneys. Nevertheless, the explicit determination of blood conductivity is particularly preferred here. For this purpose, a defined volume 6 is required, as is for example present in the interior of the (inlet) cannula 13. Accordingly, a further one to four electrodes 29, 30, 31 and 32 can be placed inside the cannula 13 (which can also be referred to as the inlet tube). Analogous to the measurement in the ventricular volume, the measurement can in this case be made by current injection and voltage measurement in electrode pairs 29 and 30, or by current injection between the electrode pair 29 and 30 and voltage measurement between the electrode pair 31 and 32. If at least one electrode 4, 5, 27 or 28 of the ventricle measurement is located in the region or near the inlet opening 12, the pair 29, 31 can be omitted. The measurement can then for example be carried out by means of a current injection in the electrode pair 27, 30 and by a voltage measurement between the electrode pair 5 and 32. Since the electrode pair 5, 27 is located in the region or near the inlet opening 12, a defined volume 6 results inside the cannula 13 between the electrode pair 5, 27 and the electrode pair 30, 32. For strictly two-point measurements, three electrodes are therefore in particular minimally necessary. The ventricular impedance measurement is then carried out by way of example between electrodes 4 and 5, and the conductivity measurement between electrodes 5 and 30.

The assignment of the electrodes shown here as current electrodes or voltage measurement electrodes is only exemplary. A current electrode in this case is in particular an electrode that can be connected or is connected to a current source. A voltage measuring electrode is in particular an electrode that can be connected or is connected to a voltage measuring device. Any assignment that can fulfill the purpose of impedance measurement (of the ventricular volume and/or conductivity) presented here is possible. The voltage source and/or the voltmeter can be part of the measuring device 9. If the current source and the voltmeter are spatially separated from the assist system 2 by an electrical supply line 18, the supply line cable particularly advantageously has a triaxial design with active shielding.

For the measurement (of the ventricular volume and/or the conductivity), alternating current can for example be injected by a current electrode, and the resulting voltage drop can for example be measured by a voltage measurement electrode. However, voltage can also be applied and the resulting current flow can be measured.

The measurement can be carried out at a single (alternating current) frequency. Values in the range of 50 kHz have been established for bioelectrical impedance analysis and impedance tomography. In addition to blood volume, the surrounding heart muscles also contribute slightly towards the measured impedance. Since this is cellular material with a structure different from the cellular material in the blood, the influence can be reduced by way of the so-called bioelectrical impedance spectroscopy. The measurement is in this case not performed at a fixed frequency, but at several frequencies. The result is the electrical impedance as a function of the frequency (cf. dispersion, Cole chart).

For example, the measurement can be carried out in the range from 1 kHz to 1 MHz. The spectroscopic measurement can for example be carried out by a sequence of sine frequencies, a so-called chirp, or a broadband binary sequence (pseudo random noise).

The ventricular impedance sampling rate should be high enough to fulfill the Nyquist theorem for expected ventricular contraction frequencies, for example 60 1/s. In contrast to a volume change of the ventricle, impedance changes of the heart muscles are only expected very slowly, so that a complete frequency range sweep is not required for every measurement. The background impedance of the heart muscle can be determined periodically. It is also advantageous to determine the frequency measurement points of the background impedance over several heartbeats. For this purpose, the measurement can be carried out at two frequencies with a high sampling rate. The first frequency is preferably fixed, the second frequency changes, for example from heartbeat to heartbeat (e.g., determined based on the impedance plot of the first frequency). The spectrum of the separate measurements is combined by way of example using the impedance plot of the first frequency. Instead of the first frequency, synchronization is for example also possible based on the pressure plot of a pressure sensor.

Figure 4:
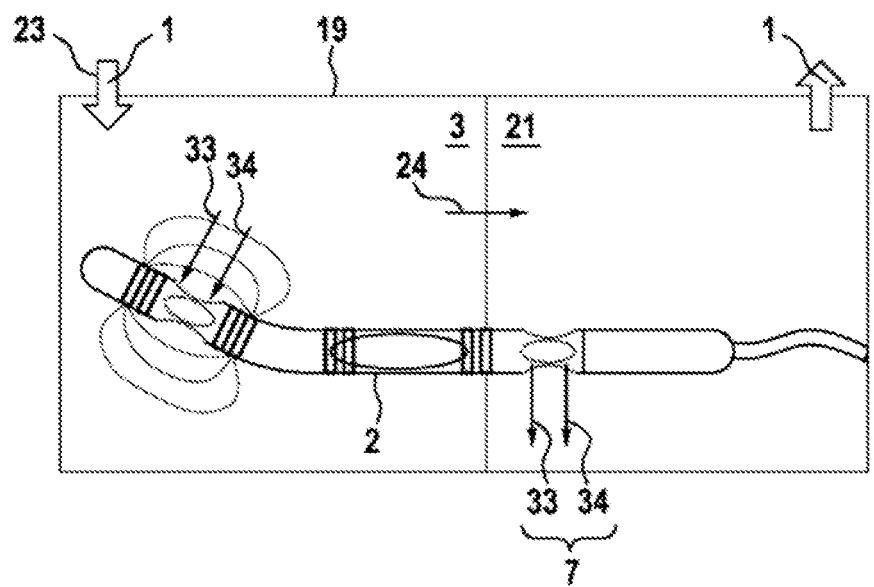

FIG. 4 shows schematically an implanted ventricular assist system 2. FIG. 4 illustrates the resulting volume flows in the heart 19. The left volume represents the ventricle or the ventricular volume 3, the right volume the aorta 21. Due to mass conservation, the (heart valve) volume flow 23 from the left atrium into the ventricle and the outflow into the aorta corresponds to the total fluid volume flow 1 or the (total) heart-time volume. Valve insufficiency or hydraulic short circuits between the ventricles are exceptions.

The assist system 2 (LVAD) conveys the circulation volume flow 33, for example by the output of a pump (not shown here) of the assist system 2. In continuous assist systems, the flow is constant; in pulsatile assist systems, this flow is time-modulated. The contraction of the ventricle causes the pressure in the ventricle to increase and the pressure difference over the assist system 2 decreases, so that the assist system 2 delivers an additional systolic volume flow 34 at constant mechanical output during the systole. If the ventricular contraction is strong enough (e.g., for short-term assistance patients), the ventricular pressure can exceed the aortic blood pressure, which leads to the opening of the aortic valve (not shown here). An additional bypass flow (formula symbol $Q_a$) is formed, which is shown in FIG. 4 as an aortic valve or bypass volume flow 24. This flow portion (bypass 24) cannot be (directly) detected by the flow sensors of the assist system 2, for example the ultrasonic sensor in the tip of the assist system 2, but essentially corresponds to the difference between the change in ventricular volume dV/dt and the pump volume flow $Q_p$. In this case, the pump volume flow $Q_p$, which only quantifies the flow through the assist system 2 itself, and which is also referred to here as fluid volume flow 7, results from the sum of the circulation volume flow 33 and the systolic volume flow 34. By combining the ventricular volume measurement over time and pump flow measurement over time, the bypass flow, i.e., the aortic valve or bypass volume flow 24 (formula symbol QA) can be determined according to the following equation:

$$Q_A(t) = \frac{\partial V}{\partial t} + Q_{P,Diastole} - Q_P(t)$$

Wherein the base pump volume flow $Q_{p,diastole}$ ($Q_p$ during the diastole) in this case corresponds to the circulation volume flow 33, and the time-dependent pump volume flow $Q_p(t)$ corresponds to the sum of the circulation volume flow 33 and the systolic volume flow 34. QA(t) corresponds to the aortic valve or bypass volume flow 24.

An exemplary derivation of this relationship as well as the heart-time volume is illustrated using the following equations 1 to 13. The formula symbols used are briefly explained first.

$Q_{HZV}$ Heart time volume
$Q_P$ Time-dependent volume flow through the pump
$Q_A$ Time-dependent volume flow through the aortic valve
$Q_V$ Time-dependent volume flow into the storage volume of the ventricle (ventricular volume change)
$Q_D$ Time-dependent volume flow from the left atrium into the aorta (assumption: base flow through the pump)
V Ventricular volume
t time $$Q_{HZV} = Q_A + Q_P \quad (1)$$

$$Q_{HZV} = Q_D + Q_V \quad (2)$$

$$Q_V = -\frac{\partial V}{\partial t} \quad (3)$$

$$Q_A + Q_P = Q_D - \frac{\partial V}{\partial t} \quad (4)$$

Assumption: $Q_D$ flows exclusively through the pump (non-pulse equivalent part of the flow). During the systole, the pulsatile portion of the flow is divided into an increased $Q_p$ and a bypass flow through the aortic valve $Q_A$:

$$Q_P = Q_D + k \cdot -\frac{\partial V}{\partial t} \quad (5)$$

$$Q_A = (1-k) \cdot -\frac{\partial V}{\partial t} \quad (6)$$

$$0 \leq k \leq 1 \quad (7)$$

The following is known from the (bio) impedance measurement:

$$Q_V(t) = -\frac{\partial V}{\partial t} \quad (8)$$

The following is known from an exemplary ultrasound measurement:

$$Q_P(t) = Q_D + k(t) \cdot -\frac{\partial V}{\partial t} \quad (9)$$

In addition, it can be assumed that the following applies during the diastole:

$$Q_{P,diastole} = Q_D \quad (10)$$

The bypass flow QA can thus be determined by:

$$Q_A(t) = Q_V(t) + Q_{P,Diastole} - Q_P(t) \quad (11)$$

and $$Q_A(t) = -\frac{\partial V}{\partial t} + Q_{P,Diastole} - Q_P(t) \quad (12)$$

In addition, the heart-time volume $Q_{HZV\ CAN\ BE}$ determined by:

$$Q_{HZV}(t) = Q_{P,Diastole} - \frac{\partial V}{\partial t} \quad (13)$$

In addition, it is also preferred to place the assist system in a specific volume measurement mode. The pump is in this case regulated by integrated pressure sensors such that the pressure at the inlet cage and the impeller cage is identical, i.e., there is no volume flow and the pump rotates only so fast that there is no return flow from the aorta through the pump into the ventricle. At the same time, the beat volume, the final diastolic blood volume and/or the contraction strength of the ventricle can be determined based on the impedance measurement data (measured therein) graph over time, and/or used to control the assist system.

In addition to volume flow, the ventricular volume 3 is also an interesting parameter. In full assistance systems (only the pump circulates blood), a suction effect or collapse of the ventricle can occur. The assist system 2 in this case circulates more blood than flows in from the left atrium. The assist system 2 (or its pump) empties the ventricle. As a result, the ventricular wall approaches the inlet cage and the assist system 2 (or its pump) can suction itself against [the ventricular wall]. If the ventricular blood pressure falls below a value of 50 mmHg, the ventricle may also collapse due to higher ambient pressures. The ventricular volume 3 can in this case be used as a control parameter in order to reduce the output of the assist system 2, in particular by reducing its circulation or pumping output, so that a minimum ventricular volume can be guaranteed.

Figure 5:
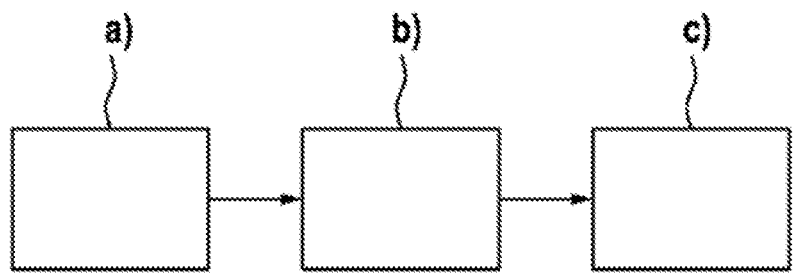

FIG. 5 shows the described method again in schematical form. The method steps a) determine a first impedance parameter at a first point in time by means of the assist system 2, b) determine a second impedance parameter at a second point in time by means of the assist system 2 and c) at least determine a change of the impedance parameter using the first impedance parameter and the second impedance parameter or compare at least the first or second impedance parameter to a threshold value are carried out in succession.

The solution proposed here in particular enables one or more of the following advantages:

Use of sensors strictly integrated in the assist system; for example, no separate ultrasound cuff is required around the aorta.

The method enables the determination of the total heart-time volume as well as the determination of the level of assistance (proportion of the pump volume flow of the total heart-time volume).

The integration of electrical impedance measurement technology is easy to implement compared to aortic ultrasonic cuffs or similar.

The total heart-time volume is measured continuously by the system, allowing the LVAD to be regulated both based on the heart-time volume as well as on the level of assistance, which is particularly advantageous in short-term assist systems (keyword weaning).

The method determines the ventricular volume, so that an assist system can be throttled, for example when a minimum ventricular volume is not reached.

The invention claimed is:

1. A method for operating an implantable cardiac assist system, the method comprising:

measuring an impedance parameter using one or more electrodes of the implantable cardiac assist system, the implantable cardiac assist system comprising a cannula configured to supply a fluid and a flow machine configured to generate a fluid flow, wherein the one or more electrodes are configured to measure an impedance parameter;

determining, by a processor of the implantable cardiac assist system, a first impedance parameter value of the impedance parameter at a first point in time measured by the one or more electrodes;

determining, by the processor, a second impedance parameter value of the impedance parameter at a second point in time different from the first point in time measured by the one or more electrodes; and determining, by the processor, a change in the impedance parameter based at least in part on the first impedance parameter value and the second impedance parameter value or comparing at least the first impedance parameter value or the second impedance parameter value to a threshold value.

2. The method of claim 1 further comprising, determining a ventricular volume based at least in part on the impedance parameter.

3. The method of claim 2, further comprising throttling the implantable cardiac assist system when the ventricular volume drops below a predetermined threshold value.

4. The method of claim 1, wherein the first impedance parameter value and the second impedance parameter value are determined by at least two electrodes arranged on the implantable cardiac assist system.

5. The method of claim 1, wherein determining the first impedance parameter value is performed at a first frequency and determining the second impedance parameter value is performed at a second frequency different from the first frequency.

6. The method of claim 1 further comprising determining fluid conductivity based at least in part on the first impedance parameter value and the second impedance parameter value, and wherein determining the first impedance parameter value and determining the second impedance parameter value is performed in a defined volume of the implantable cardiac assist system.

7. The method of claim 1 further comprising determining a fluid volume flow that flows through the implantable cardiac assist system.

8. The method of claim 1 further comprising determining a total fluid volume flow in a region of the implantable cardiac assist system.

9. An implantable cardiac assist system comprising:
a cannula configured to supply a fluid;
a flow machine configured to generate a fluid flow;
one or more electrodes configured to measure an impedance parameter;
a processor; and
a computer-readable storage device storing therein computer-readable instructions that, when executed by the processor, cause the processor to:
receive the impedance parameter from the one or more electrodes;
determine a first impedance parameter value of the impedance parameter at a first point in time;
determine a second impedance parameter value of the impedance parameter at a second point in time different from the first point in time; and
determine a change in the impedance parameter based at least in part on the first impedance parameter value and the second impedance parameter value, or compare at least the first impedance parameter value or the second impedance parameter value to a threshold value.

10. The system of claim 9, wherein the processor is further configured to determine a ventricular volume based at least in part on the impedance parameter.

11. The system of claim 9, wherein the processor is further configured to determine fluid conductivity based at least in part on the first impedance parameter value and the second impedance parameter value, and wherein determining the first impedance parameter value and determining the second impedance parameter value is performed in a defined volume of the implantable cardiac assist system.

12. The system of claim 9, wherein the processor is configured to determine the first impedance parameter value at a first frequency, and wherein the processor is configured to determine the second impedance parameter value at a second frequency different from the first frequency.

13. An implantable cardiac assist system comprising:
a cannula configured to supply a fluid;
a flow machine configured to generate a fluid flow;
a measuring device configured to measure an impedance parameter; and
a processing unit configured to determine a first impedance parameter value of the impedance parameter at a first point in time and a second impedance parameter value of the impedance parameter at a second point in time and to determine a change in the impedance parameter based at least in part on the first impedance parameter value and the second impedance parameter value or to compare the first impedance parameter value or the second impedance parameter value to a threshold value,
wherein the measuring device comprises at least two electrodes configured to measure a ventricular impedance associated with the implantable cardiac assist system, wherein the at least two electrodes are arranged circumferentially on or in an outer surface of the implantable cardiac assist system.

14. The system of claim 13, wherein the measuring device is configured to determine impedance at different frequencies.

15. The system of claim 13, wherein the at least two electrodes are arranged circumferentially on an outer surface of the cannula.

16. The system of claim 13, wherein the at least two electrodes are configured to be positioned in an area of a ventricle of a heart when the implantable cardiac assist system is implanted.

17. The system of claim 13, further comprising a device for determining a fluid volume flow.

18. The system of claim 17, wherein the device for determining the fluid volume flow is an ultrasonic sensor.

* * * * *